(12) United States Patent
Sharma et al.

(10) Patent No.: US 8,247,530 B2
(45) Date of Patent: Aug. 21, 2012

(54) N-ALKYLATED CYCLIC PEPTIDE MELANOCORTIN AGONISTS

(75) Inventors: Shubh D. Sharma, Cranbury, NJ (US); Yi-Qun Shi, East Brunswick, NJ (US); Kevin D. Burris, Washington Crossing, PA (US); Annette Shadiack, Somerset, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 1688 days.

(21) Appl. No.: 11/557,408

(22) Filed: Nov. 7, 2006

(65) Prior Publication Data

US 2011/0009341 A1    Jan. 13, 2011

Related U.S. Application Data

(60) Provisional application No. 60/734,734, filed on Nov. 8, 2005.

(51) Int. Cl.
*A61K 38/16* (2006.01)
*A61K 38/00* (2006.01)

(52) U.S. Cl. .................. 530/312; 514/10.7; 514/21.8

(58) Field of Classification Search .................. None
See application file for complete search history.

(56) References Cited

U.S. PATENT DOCUMENTS

| | | | |
|---|---|---|---|
| 5,576,290 A | 11/1996 | Hadley | |
| 5,674,839 A | 10/1997 | Hruby et al. | |
| 5,693,608 A | 12/1997 | Bechgaard et al. | |
| 5,714,576 A | 2/1998 | Hruby et al. | |
| 5,908,825 A | 6/1999 | Fasano et al. | |
| 5,977,070 A | 11/1999 | Piazza et al. | |
| 6,051,555 A | 4/2000 | Hadley | |
| 6,284,735 B1 | 9/2001 | Girten et al. | |
| 6,579,968 B1 | 6/2003 | Blood et al. | |
| 6,632,419 B2 * | 10/2003 | Rubsamen et al. | 424/43 |
| 6,794,489 B2 | 9/2004 | Blood et al. | |
| 7,399,613 B2 * | 7/2008 | DeFrees et al. | 435/89 |
| 7,416,858 B2 * | 8/2008 | DeFrees et al. | 435/68.1 |
| 2001/0056179 A1 | 12/2001 | Chen et al. | |
| 2002/0004512 A1 | 1/2002 | Bakshi et al. | |
| 2006/0293223 A1 | 12/2006 | Gadski et al. | |
| 2007/0027091 A1 | 2/2007 | Conde-Frieboes et al. | |
| 2007/0123453 A1 | 5/2007 | Heiman et al. | |

FOREIGN PATENT DOCUMENTS

| | | |
|---|---|---|
| WO | WO 02/26774 | 4/2002 |
| WO | WO 03/006620 | 1/2003 |
| WO | WO 2005/000338 | 1/2005 |
| WO | WO 2005/030797 | 4/2005 |
| WO | WO 2006/048449 | 5/2006 |
| WO | WO 2006/048450 | 5/2006 |

OTHER PUBLICATIONS

Hadley et. al., Biological Activities of Melanotropic Peptide Fatty acid Conjugates, Pigment Cell Research, 4:180-185 (1991).*
(Biological Activities of Melanotropic Peptide Fatty acid Conjugates Pigment Cell Research, 4:180-185 1991, p. 180, col. 1 ).*
Miklos Löw et al., Role of chain termini in selective steroidogenic effect of ACTH/MSH (4-10) on isolated adrenocortical cells, Peptides 11:29-31, 1990.
Maria A. Bednarek et al., Structure-function studies on the cyclic peptide MT-II, lactam derivative of α-melanotropin, Peptides 20:401-409 (1999).

* cited by examiner

*Primary Examiner* — Christina Bradley
*Assistant Examiner* — Jeanette Lieb
(74) *Attorney, Agent, or Firm* — Stephen A. Slusher

(57) ABSTRACT

A melanocortin-4 receptor agonist cyclic peptide of the formula

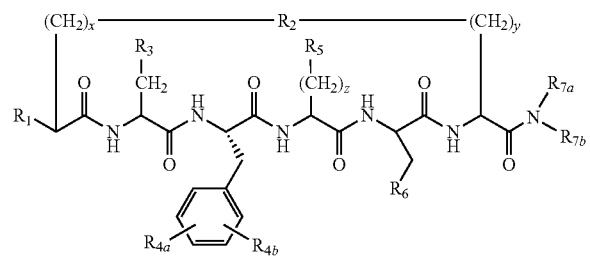

where $R_1$, $R_2$, $R_3$, $R_{4a}$, $R_{4b}$, $R_5$, $R_6$, $R_{7a}$, $R_{7b}$, x, y and z are as defined in the specification, and a method of treating sexual dysfunction, including male erectile dysfunction and female sexual dysfunction, and other melanocortin 4 receptor responsive conditions and disorders.

20 Claims, No Drawings

N-ALKYLATED CYCLIC PEPTIDE MELANOCORTIN AGONISTS

CROSS-REFERENCE TO RELATED APPLICATIONS

This application claims priority to and the benefit under 35 USC §119(e) of U.S. Provisional Patent Application Ser. No. 60/734,734, entitled "N-Alkylated Cyclic Peptide Melanocortin Agonists", filed on Nov. 8, 2005, and the specification and claims thereof are incorporated here by reference.

BACKGROUND OF THE INVENTION

1. Field of the Invention (Technical Field)

The present invention relates to C-terminus N-alkylated cyclic peptides that are agonists for the melanocortin-4 receptor (MC4-R), and which may be used in the treatment of sexual dysfunction and other conditions.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Melanocortin Receptors.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain. Inactivation of this receptor by gene targeting has been reported to result in mice with the maturity-onset obesity syndrome that is associated with hyperphagia, hyperinsulinemia, and hyperglycemia (Huszar D, Lynch C A, Fairchild-Huntress V, et al. Targeted disruption of the melanocortin-4 receptor results in obesity in mice. *Cell* 88:131-141, 1997). MC4-R is a molecular target for therapeutic intervention in energy homeostasis.

Compounds specific for MC4-R, and secondarily compounds specific for MC3-R or MC5-R, are believed to be useful in regulation of mammalian energy homeostasis, including use as agents for attenuating food intake and body weight gain. MC4-R agonists are believed to be useful for treating sexual dysfunction, including male erectile dysfunction, and for decreasing food intake and body weight gain, such as for treatment of obesity. Such compounds may also be employed for treatment of depression and related disorders, decreasing voluntary ethanol consumption, and the like. MC4-R antagonists, by contrast, are believed to be useful for weight gain aid, such as for use in treatment of cachexia, sarcopenia, wasting syndrome or disease, and anorexia.

Sexual Dysfunction.

Sexual dysfunction, including both penile erectile dysfunction or impotence and female sexual dysfunction, is a common medical problem. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, commonly used orally administered drugs for treatment of sexual dysfunction in the male are phosphodiesterase 5 (PDE-5) inhibitors, increasing the persistence of cyclic guanosine monophosphate and thereby enhancing erectile response. Such drugs include Viagra®, a brand of sildenafil, Levitra®, a brand of monohydrochloride salt of vardenafil, and Cialis®, a brand of tadalafil. Another drug approved in Europe for treating male erectile dysfunction is Ixense®, a brand of apomorphine that is a non-selective dopa receptor agonist. Oral and nasal formulations of apomorphine have undergone clinical evaluation. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin $E_1$, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A number of other agents have been shown to induce or facilitate penile erection in laboratory animals. These include very diverse classes of ligands such as oxytocin (Benelli A., Poggioli R., Luppi P., Ruini L., Bertolini A., Arletti R., Oxytocin enhances, and oxytocin antagonism decreases, sexual receptivity in intact female rats. *Neuropeptides* 27:245-50 (1994)), vasopressin, vasoactive intestinal peptide, melanotropins, and ACTH as well as their analogs.

A variety of treatments have also been explored for female sexual dysfunction, including use of sildenafil, although the Food and Drug Administration has not specifically approved such use. Testosterone propionate has also been employed to increase or augment female libido.

Melanocortin Agonist Peptides.

Melanocortin receptor-specific compounds have been explored for use of treatment of sexual dysfunction. In one report, a cyclic α-melanocyte-stimulating hormone ("α-MSH") analog, Ac-Nle-cyclo(-Asp-His-D-Phe-Arg-Trp-Lys)-NH$_2$, was evaluated for erectogenic properties for treatment of men with erectile dysfunction. Wessells H. et al., *J Urology* 160:389-393 (1998); see also U.S. Pat. No. 5,576,290, issued Nov. 19, 1996 to M. E. Hadley, entitled Compositions and Methods for the Diagnosis and Treatment of Psychogenic Erectile Dysfunction and U.S. Pat. No. 6,051,555, issued Apr. 18, 2000, also to M. E. Hadley, entitled Stimulating Sexual Response in Females. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled Cyclic Analogs of Alpha-MSH Fragments, and in U.S. Pat. No. 5,714,576, issued Feb. 3, 1998, to V. J. Hruby, M. E. Hadley and F. Al-Obeidi, entitled Linear Analogs of Alpha-MSH Fragments.

Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. These peptides are related to the structure of melanocortins. Other peptides are disclosed in U.S. Pat. No. 6,284,735 and U.S. Published Patent Applications Nos. 2001/0056179 and 2002/0004512.

The peptide Ac-Nle-cyclo(-Asp-His-D-Phe-Arg-Trp-Lys)-OH is disclosed in U.S. Pat. No. 6,579,968, issued Jun. 17, 2003, and U.S. Pat. No. 6,794,489, Sep. 21, 2004, and is employed for treatment of erectile dysfunction and female sexual dysfunction.

It is believed that erectile response to melanocortin receptor-specific compounds, and both male and female sexual response in general, is at least in part related to the central tetrapeptide sequence, His$^6$-Phe$^7$-Arg$^8$-Trp$^9$ (SEQ ID NO:1) of native α-MSH. In general, all natural melanocortin peptides share the same active core sequence, His-Phe-Arg-Trp (SEQ ID NO:1), including melanotropin neuropeptides and adrenocorticotropin. While the mechanism of His-Phe-Arg-Trp (SEQ ID NO:1) induction of erectile response has not been fully elucidated, it is generally accepted that it involves the central nervous system, and binding to MC3-R and/or MC4-R, and according to most researchers, MC4-R.

Both cyclic and linear α-MSH peptides have been studied for sexual dysfunction; however, the peptides heretofore evaluated have had an —NH$_2$ group at the C-terminus, or, as in the case of Ac-Nle-cyclo(-Asp-His-D-Phe-Arg-Trp-Lys)-OH, an —OH group.

In certain aspects, this application is related to U.S. patent application Ser. No. 11/174,845, filed Jul. 5, 2005, entitled "Cyclic Peptides for Treatment of Cachexia", to Shubh D. Sharma, et al., which claimed priority to U.S. Provisional Patent Application Ser. No. 60/585,971, entitled "Cyclic Peptides for Treatment of Cachexia", to Shubh D. Sharma, et al.; and to U.S. patent application Ser. No. 10/638,071, filed Aug. 8, 2003, entitled "Cyclic Peptide Compositions and Methods for Treatment of Sexual Dysfunction", to Shubh D. Sharma, et al., which is a continuation-in-part of International Application No. PCT/US02/22196, International Publication No. WO 03/006620, filed on Jul. 11, 2002, entitled "Linear and Cyclic Melanocortin Receptor-Specific Peptides", to Shubh D. Sharma, et al., which claimed priority to U.S. Provisional Patent Application Ser. No. 60/304,836, entitled "Linear and Cyclic Melanocortin Receptor-Specific Peptides", filed on Jul. 11, 2001, and the specification and claims thereof of each are incorporated herein by reference.

BRIEF SUMMARY OF THE INVENTION

In one embodiment the invention provides a cyclic peptide of structural formula (I):

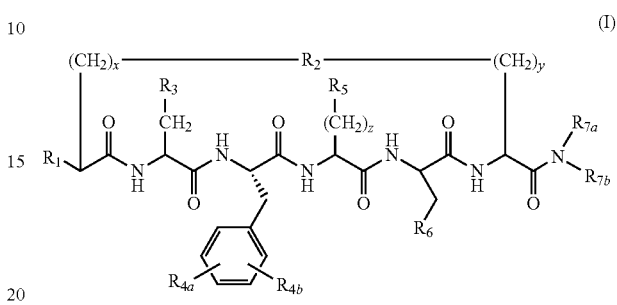

wherein:

R$_1$ is H, NH$_2$,

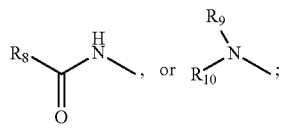

R$_2$ is —C(=O)—NH—, —NH—C(=O)—, —S—, or —S—S—,

R$_3$ is 4-imidazolyl or 3-indolyl;

R$_{4a}$ and R$_{4b}$ are each optional ring substituents, and when one or both are present, are the same or different and independently hydroxyl, halogen, alkyl, or aryl groups attached directly or through an ether linkage;

R$_5$ is —NH$_2$ or —NH(C=NH)NH$_2$;

R$_6$ is 1- or 2-naphthyl or 3-indolyl, optionally with one or two ring substituents, and when one or both ring substitutents are present, are the same or different and independently hydroxyl, halogen, alkyl, or aryl groups attached directly or through an ether linkage;

R$_{7a}$ and R$_{7b}$ are each independently H or a C$_1$ to C$_4$ linear or branched alkyl chain, on the proviso that both R$_{7a}$ and R$_{7b}$ are not H;

R$_8$ is H, NH$_2$, a lower aliphatic C$_1$ to C$_4$ branched or linear alkyl chain, a C$_1$ to C$_4$ aralkyl, or a C$_1$ to C$_4$ omega amino aliphatic chain;

R$_9$ is H, a lower aliphatic C$_1$ to C$_4$ branched or linear alkyl chain, a C$_1$ to C$_4$ aralkyl, or a C$_1$ to C$_4$ omega amino aliphatic chain;

R$_{10}$ is an aliphatic L- or D-amino acid, an N-acylated L- or D-amino acid or a linear or branched C$_1$ to C$_{17}$ alkyl, aryl, heteroaryl, alkene, alkenyl, or aralkyl chain;

x is 1 to 4, and y is 1 to 5, provided that x+y is 2 to 7; and z is 1 to 5.

In another embodiment, there is provided a cyclic peptide of structural formula (II):

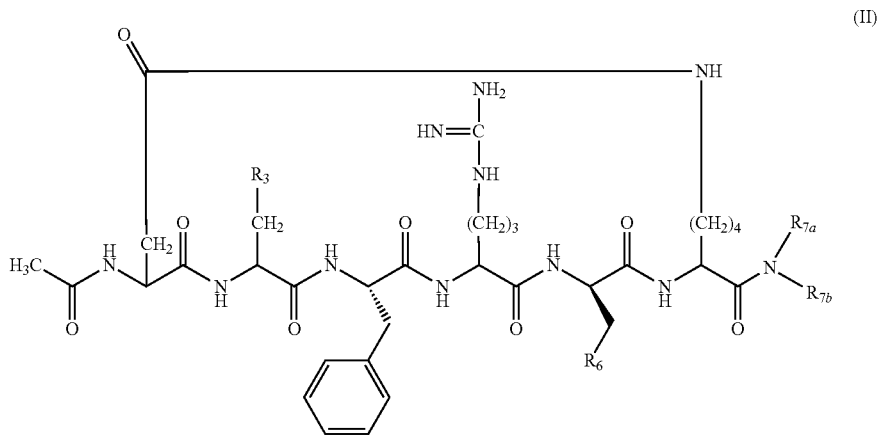

(II)

wherein $R_3$, $R_6$, $R_{7a}$ and $R_{7b}$ are as defined for the cyclic peptides of structural formula (I).

The cyclic peptides of structural formula (II) include any of the following cyclic peptides:

```
Ac-cyclo(-Asp-His-D-Phe-Arg-Trp-Lys)-N(CH₃)₂,

Ac-cyclo(-Asp-His-D-Phe-Arg-Trp-Lys)-NH-CH₂-CH₃,

Ac-cyclo(-Asp-Trp-D-Phe-Arg-Nal 1-Lys)-NH-CH₂-CH₃,

Ac-cyclo(-Asp-Trp-D-Phe-Arg-Nal 1-Lys)-N(CH₃)₂,

Ac-cyclo(-Asp-His-D-Phe-Arg-Nal 1-Lys)-NH-CH₂-CH₃,
or

Ac-cyclo(-Asp-His-D-Phe-Arg-Nal 1-Lys)-N(CH₃)₂.
```

In another embodiment, there is provided acyclic peptide of structural formula (III):

wherein $R_3$, $R_6$, $R_{7a}$ and $R_{7b}$ are as defined for the cyclic peptides of structural formula (I).

The cyclic peptides of structural formula (III) include any of the following cyclic peptides:

```
Ac-Nle-cyclo(-Asp-His-D-Phe-Arg-Trp-Lys)-
NH-CH₂-CH₃,

Ac-Nle-cyclo(-Asp-His-D-Phe-Arg-Trp-Lys)-N(CH₃)₂,

Ac-Nle-cyclo(-Asp-His-D-Phe-Arg-Nal 1-Lys)-
NH-CH₂-CH₃,

Ac-Nle-cyclo(-Asp-Trp-D-Phe-Arg-Nal 1-Lys)-
N(CH₃)₂,

Ac-Nle-cyclo(-Asp-His-D-Phe-Arg-Nal 1-Lys)-
NH-CH₂-CH₃,
or

Ac-Nle-cyclo(-Asp-Trp-D-Phe-Arg-Nal 1-Lys)-NH-
CH₂-CH₃.
```

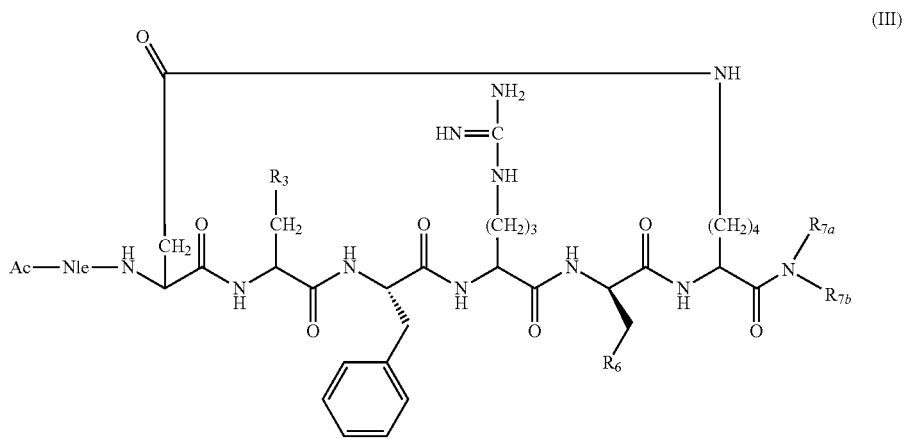

(III)

In yet another embodiment, there is provided a cyclic peptide of structural formula (IV):

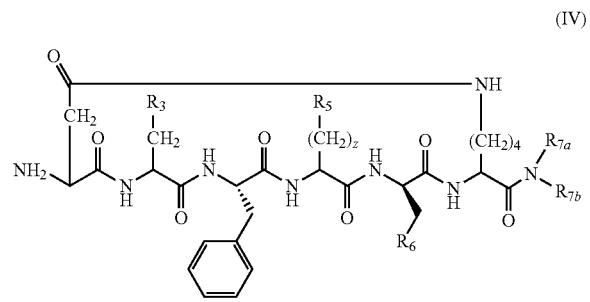

(IV)

wherein $R_3$, $R_5$, $R_6$, $R_{7a}$, $R_{7b}$ and z are as defined for the cyclic peptides of structural formula (I).

The cyclic peptides of structural formula (IV) include any of the following cyclic peptides:

```
H-cyclo(-Asp-His-D-Phe-Arg-Trp-Lys)-N(CH3)2,

H-cyclo(-Asp-His-D-Phe-Arg-Trp-Lys)-NH-CH2-CH3,

H-cyclo(-Asp-Trp-D-Phe-Arg-Nal 1-Lys)-NH-CH2-CH3,

H-cyclo(-Asp-Trp-D-Phe-Arg-Nal 1-Lys)-N(CH3)2,

H-cyclo(-Asp-His-D-Phe-Arg-Nal 1-Lys)-NH-CH2-CH3,
or

H-cyclo(-Asp-His-D-Phe-Arg-Nal 1-Lys)-N(CH3)2.
```

The invention further provides a pharmaceutical preparation, comprising a cyclic peptide of any of formulas (I), (II), (III) or (IV), or a pharmaceutically acceptable salt thereof, and a pharmaceutically acceptable carrier.

The invention further provides a method of treating sexual dysfunction, comprising administering to a mammal a pharmaceutically sufficient amount of a pharmaceutical preparation comprising a cyclic peptide of any of formulas (I), (II), (III) or (IV), or a pharmaceutically acceptable salt thereof, and a pharmaceutically acceptable carrier.

The invention further provides a method of treating obesity and related energy homeostasis disorders, comprising administering to a mammal a pharmaceutically sufficient amount of a pharmaceutical preparation comprising a cyclic peptide of any of formulas (I), (II), (III) or (IV), or a pharmaceutically acceptable salt thereof, and a pharmaceutically acceptable carrier.

In another embodiment the invention provides a cyclic hexapeptide with a C-terminus N-alkyl group, wherein the N-alkyl group comprises one or two $C_1$ to $C_4$ linear or branched alkyl chains, the hexapeptide containing the core sequence His-D-Phe-X—Y or Trp-D-Phe-X—Y, wherein X is an L-amino acid selected from the group consisting of Arg, Lys, Orn, Harg and Hlys and Y is an L- or D-amino acid selected from the group consisting of Nal 1, Nal 2 and Trp, and wherein any aromatic ring in the core sequence may optionally include one or two ring substituents, and when one or both ring substitutents are present, are the same or different and independently hydroxyl, halogen, alkyl, or aryl groups attached directly or through an ether linkage. In one aspect of this embodiment, the cyclic hexapeptide has an N-terminus Ac or $NH_2$ group. In another aspect of this embodiment, the cyclic hexapeptide is cyclized by formation of an amide bond between an amino group of a side chain of an amino acid in the 1 position or an amino group of the N-terminus group of the amino acid in the 1 position and a side chain carboxyl group of an amino acid residue at the 6 position. In another aspect of this embodiment, the hexapeptide is cyclized by formation of an amide bond between a side chain carboxyl group of an amino acid residue in the 1 position and an amino group of a side chain of an amino acid at the 6 position. In another aspect of this embodiment, the hexapeptide is cyclized by formation of a covalent bond comprising an amide, disulfide, thioether, Schiff base, reduced Schiff base, imide, secondary amine, carbonyl, urea, hydrazone or oxime bond. In another aspect of this embodiment, the core sequence is in the 2 to 5 positions and is either His-D-Phe-X-Nal 1 or His-D-Phe-X-Nal 2 and is cyclized through the amino acids in the 1 and 6 positions. In another aspect of this embodiment, the core sequence is in the 2 to 5 positions and is either Trp-D-Phe-X-Nal 1 or His-D-Phe-X-Nal 2 and is cyclized through the amino acids in the 1 and 6 positions. In another aspect of this embodiment, the core sequence is in the 2 to 5 positions and is His-D-Phe-X-Trp, and is cyclized through the amino acids in the 1 and 6 positions. In each of the foregoing aspects of this embodiment, D-Phe may be substituted with one, two or more substituents, and thus D-Phe includes any D-isomer of a phenylalanine wherein the phenyl ring is substituted with one or more ring substituents independently selected from the group consisting of hydroxyl, halogen, sulfonamide, alkyl or aryl groups attached directly or through an ether linkage. D-Phe may further be and includes D-phenylglycine and D-homophenylalanine, optionally with one or more ring substituents as described. D-Phe may be, for example, selected from the group consisting of D-isomers of Phe(2-Cl), Phe(3-Cl), Phe(4-Cl), Phe(5-Cl), Phe(2,4-diCl), Phe(2,4-diF), Phe(3,4-diCl), Phe(4-NO₂), Phe(4-Me), Phe(4-OMe), Phe(4-F), Phe(4-F), Phe(4-Br), Phe(4-CF₃), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-CF₃), Phe(4-CN) and Phe(3,4-di-OMe).

Cyclic peptides of the foregoing formulas may be separated into their individual diastereoisomers by any means known in the art, including but not limited to fractional crystallization from a suitable solvent, such as methanol or ethyl acetate or a mixture thereof, or by chiral chromatography using an optically active stationary phase. It is also possible to synthesize a specific diastereoisomer of a cyclic peptide of any of the foregoing formulas by stereospecific synthesis using optically pure starting materials or reagents of known configuration. In a preferred embodiment, the cyclic peptides of the foregoing formulas are synthesized using reagents of known configurations, and accordingly have a specific diastereoisomeric form.

In one embodiment, the cyclic peptide is one of the following:

```
Ac-cyclo(-Asp-His-D-Phe-Arg-Trp-Lys)-N(CH3)2,

Ac-cyclo(-Asp-His-D-Phe-Arg-Trp-Lys)-NH-CH2-CH3,

Ac-cyclo(-Asp-Trp-D-Phe-Arg-Nal 1-Lys)-NH-CH2-CH3,

Ac-cyclo(-Asp-Trp-D-Phe-Arg-Nal 1-Lys)-N(CH3)2,

Ac-cyclo(-Asp-His-D-Phe-Arg-Nal 1-Lys)-NH-CH2-CH3,

Ac-cyclo(-Asp-His-D-Phe-Arg-Nal 1-Lys)-N(CH3)2,

Ac-Nle-cyclo(-Asp-His-D-Phe-Arg-Trp-Lys)-
NH-CH2-CH3,
```

```
Ac-Nle-cyclo(-Asp-His-D-Phe-Arg-Trp-Lys)-N(CH3)2,

Ac-Nle-cyclo(-Asp-His-D-Phe-Arg-Nal 1-Lys)-
NH-CH2-CH3,

Ac-Nle-cyclo(-Asp-Trp-D-Phe-Arg-Nal 1-Lys)-
N(CH3)2,

Ac-Nle-cyclo(-Asp-His-D-Phe-Arg-Nal 1-Lys)-
NH-CH2-CH3,

Ac-Nle-cyclo(-Asp-Trp-D-Phe-Arg-Nal 1-Lys)-
NH-CH2-CH3,

H-cyclo(-Asp-His-D-Phe-Arg-Trp-Lys)-N(CH3)2,

H-cyclo(-Asp-His-D-Phe-Arg-Trp-Lys)-NH-CH2-CH3,

H-cyclo(-Asp-Trp-D-Phe-Arg-Nal 1-Lys)-NH-CH2-CH3,

H-cyclo(-Asp-Trp-D-Phe-Arg-Nal 1-Lys)-N(CH3)2,

H-cyclo(-Asp-His-D-Phe-Arg-Nal 1-Lys)-NH-CH2-CH3,
or

H-cyclo(-Asp-His-D-Phe-Arg-Nal 1-Lys)-N(CH3)2.
```

In another embodiment, the cyclic peptide is one of the following:

```
Ac-cyclo(-Asp-Trp-D-Phe-Arg-Nal 2-Lys)-NH-CH2-CH3,

Ac-cyclo(-Asp-Trp-D-Phe-Arg-Nal 2-Lys)-N(CH3)2,

Ac-cyclo(-Asp-His-D-Phe-Arg-Nal 2-Lys)-NH-CH2-CH3,

Ac-cyclo(-Asp-His-D-Phe-Arg-Nal 2-Lys)-N(CH3)2,

Ac-Nle-cyclo(-Asp-His-D-Phe-Arg-Nal 2-Lys)-
NH-CH2-CH3,

Ac-Nle-cyclo(-Asp-Trp-D-Phe-Arg-Nal 2-Lys)-
N(CH3)2,

Ac-Nle-cyclo(-Asp-His-D-Phe-Arg-Nal 2-Lys)-
NH-CH2-CH3,

Ac-Nle-cyclo(-Asp-Trp-D-Phe-Arg-Nal 2-Lys)-
NH-CH2-CH3,

H-cyclo(-Asp-Trp-D-Phe-Arg-Nal 2-Lys)-NH-CH2-CH3,

H-cyclo(-Asp-Trp-D-Phe-Arg-Nal 2-Lys)-N(CH3)2,

H-cyclo(-Asp-His-D-Phe-Arg-Nal 2-Lys)-NH-CH2-CH3,
or

H-cyclo(-Asp-His-D-Phe-Arg-Nal 2-Lys)-N(CH3)2.
```

A primary object of the present invention is to provide a peptide-based melanocortin receptor-specific pharmaceutical, wherein the peptide is a selective MC4-R agonist, for use in treatment of sexual dysfunction and other MC4-R associated disorders.

Another object of the invention is to provide a peptide-based melanocortin receptor-specific pharmaceutical for use in treatment of sexual dysfunction wherein the peptide has a C-terminus N-alkyl group.

Another object of this invention is to provide peptides which are specific for melanocortin receptor MC4-R and which are agonists.

Another object of the present invention is a peptide-based melanocortin receptor-specific pharmaceutical for use in treatment of obesity and other energy homeostasis disorders.

Yet another object of the present invention is to provide a melanocortin receptor-specific pharmaceutical for use in treatment wherein administration of the treatment is via nasal administration.

According to one embodiment of the present invention, there is provided a C-terminus N-alkyl cyclic peptide that is a specific MC4-R agonist suitable for use as a specific pharmaceutical in treatment of sexual dysfunction and which is efficacious at low doses.

Another aspect of the present invention provides a specific MC4-R cyclic peptide agonist that is effective over a significant dose range.

Yet another aspect of the present invention provides specific MC4-R cyclic peptide agonists for use in treatment of eating disorders which, because of increased efficacy at low doses, may be administered by delivery systems other than art conventional intravenous, subcutaneous or intramuscular injection, including but not limited to oral delivery systems, nasal delivery systems and mucous membrane delivery systems.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended provisional claims.

DETAILED DESCRIPTION OF THE INVENTION

Definitions

Certain terms as used throughout the specification and claims are defined as follows.

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. In addition, the following abbreviations have the meanings giving:

Harg—Homoarginine
Hlys—Homolysine
Nal 1-3—(1-naphthyl)alanine
Nal 2-3—(2-naphthyl)alanine
(N-Bzl)Nal 2—N-benzyl-3-(2-naphthyl) alanine
2-Naphthylacetyl—2-naphthyl-$CH_2CO$—
Phe(4-F)—para-fluoro-phenylalanine
Phe(4-Br)—4-bromo-phenylalanine
Phe(4-$CF_3$)—4-trifluoromethyl-phenylalanine
Phe(4-Cl)—4-chloro-phenylalanine
Phe(3-Cl)—3-chloro-phenylalanine
Phe(2-Cl)—2-chloro-phenylalanine
Phe(2,4-diCl)—2,4,-dichloro-phenylalanine
Phe(2,4-diF)—2,4-difluoro-phenylalanine
Phe(3,4-diCl)—3,4,-dichloro-phenylalanine
Phe(5-Cl)—5-chloro-phenylalanine
Phe(2-Cl,4-Me)—2-chloro-4-methyl-phenylalanine
Phe(2-Me,4-Cl)—4-chloro-2-methyl-phenylalanine
Phe(2-F,4-Cl)—4-chloro-2-fluoro-phenylalanine
Phe(2,4-diMe)—2,4-dimethyl-phenylalanine
Phe(2-Cl,4-$CF_3$)—2-chloro-4-trifluoromethyl-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylalanine
Phe(4-OMe)—4-methoxy-phenylalanine
Phe(4-CN)—4-cyano-phenylalanine
Phe(4-$NO_2$)—4-nitro-phenylalanine In the listing of peptides according to the present invention, conventional amino acid residues have their conventional meaning as given in Chapter 2400 of the *Manual of Patent Examining Procedure*, $8^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Tyr" is tyrosine, "Ser" is serine and so on.

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substitutent of an alkane.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond; examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkylthio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—, referred to herein as "Ac".

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino aliphatic chain" includes an aliphatic moiety with a terminal amino group. Examples of omega amino aliphatic chains include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as for example methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —$CF_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a peptide of the present invention and a pharmaceutically acceptable carrier.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

By a melanocortin receptor "agonist" is meant a naturally occurring substance or manufactured drug substance or composition that can interact with a melanocortin receptor and initiate a pharmacological response characteristic of the melanocortin receptor. By a melanocortin receptor "antagonist" is meant a naturally occurring substance or manufactured drug substance or composition that opposes the melanocortin receptor-associated responses normally induced by a melanocortin receptor agonist agent. By a melanocortin receptor "inverse agonist" is meant a drug or a compound that stabilizes the inactive conformation of the melanocortin receptor and inhibits basal activity.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

Positions of amino acids in peptides are determined in the conventional manner, by counting amino acid residue positions from the N-terminus to the C-terminus. Chemical structures shown herein are prepared using conventional software, and any open valancy appearing on a carbon, oxygen or nitrogen atom in the structures herein indicates the presence of a hydrogen.

Cyclic Peptides of the Invention

In one embodiment the invention provides N-alkylated α-MSH cyclic peptides, which are cyclic peptides that include the core α-MSH sequence His-Phe-Arg-Trp (SEQ ID NO:1), His-D-Phe-Arg-Trp, or homologs or analogs of either of the foregoing, in which the peptide is N-alkylated, which is to say that it terminal nitrogen with one or two linear or branched alkyl chains. In a preferred embodiment, the N-alkylated α-MSH cyclic peptides of this invention have a C-terminus group which is —NH—$CH_3$, —NH—$CH_2$—$CH_3$, —NH—$CH_2$—$CH_2$—$CH_3$, —N($CH_3$)$_2$, —N($CH_2$—$CH_3$)$_2$, —NH—CH—($CH_3$)$_2$, or —NH—$CH_2$—CH—($CH_3$)$_2$.

In another aspect, the invention provides certain N-alkylated cyclic peptides, specific for one or more melanocortin receptors, and which in some embodiments are an agonist with respect to such receptor or receptors. However, the peptides of this invention need not be agonists, and need not have significant specificity for any one given melanocortin receptor. In general, there is no rank order correlation between affinity for a given receptor, such as MC4-R, measured by either competitive inhibition with α-MSH or an analog, such as NDP-MSH, including $K_i$ value, and effectiveness for treatment of sexual dysfunction. Such peptides can preferably be employed in the treatment of sexual dysfunction, and may be characterized in part as inducing an erectile response in mammalian males, including but not limited to rodents.

Homologs of the cyclic peptide include those sequences with a single amino acid substitution at any location. In one embodiment of the invention, the substitution is made by any of the naturally occurring amino acids or unnaturally occurring amino acids. In a preferred embodiment the substitution is made by Phe, Lys, Trp, Tyr, Phe(4-Cl), Orn, Nal 1, Nal 2, or Bip. Homologs of the peptide may also include those sequences where one amino acid with an aromatic ring has been substituted for another amino acid with a different aromatic ring. An example of this substitution would be replacing a Phe residue with a Trp residue. Homologs of the peptide may also include those sequences where an amino acid with a charged side chain is replaced by another amino acid with or without a charged side chain. Examples of this include, without limitation, replacing an Arg residue (positively charged side chain) with a Lys (positively charged side chain) or replacing a His (positively charged side chain) with a Phe (nonpolar side chain).

Another aspect of the present invention provides certain cyclic peptides having a C-terminus N-alkyl group, which cyclic peptides are specific for one or more melanocortin receptors, preferably MC4-R, and alternatively MC4-R and MC3-R. Most preferably the N-alkylated cyclic peptides bind to MC4-R with high affinity, with a Ki value of at least 100 nM, preferably of at least 10 nM and most preferably from about 0.01 nM to about 2 nM.

A cyclic peptide can be obtained by inducing the formation of a covalent bond between an amino group at the N-terminus of the peptide, if provided, and a carboxyl group of a reactive amino acid side chain moiety, if provided. A cyclic peptide can also be obtained by forming a covalent bond between a terminal reactive group and a reactive amino acid side chain moiety, or between two reactive amino acid side chain moieties. A cyclic peptide can also be obtained by forming a disulfide covalent bond between two sulfhydryl group containing amino acid side chain moieties or a terminal sulfhydryl group and a sulfhydryl group in another amino acid side chain moiety. Peptides with lanthionine, cystathionine, or penthionine covalent bonds can also be formed, such as cyclic bonds formed from cysteine, homocysteine or penicillamine amino acid residues. These bonds are thioether-bridged bonds. Galande, A. K. and Spatola, A. F. *Lett. Pept. Sci.* 8, 247 (2001), is incorporated herein by reference. Thus a cyclic peptide can also be obtained by forming a thioether covalent bond between two reactive amino acid side chain moieties or between a terminal reactive group and a reactive amino acid side chain moiety. One skilled in the art would know that the means by which a given peptide is made cyclic is determined by the reactive groups present in the peptide and the desired characteristics of the peptide.

The peptides of the invention are further characterized in that they are preferable not antagonists for any MC receptor, and are preferably inactive, agonists or partial agonists as to all MC receptors other than MC4-R. All peptides of the invention are functional agonists as to MC4-R.

Peptide Synthesis

The cyclic peptides of this invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected. In a preferred conventional procedure, the cyclic peptides of this invention may be synthesized by solid-phase synthesis and purified according to methods known in the art. Any of a number of well-known procedures utilizing a variety of resins and reagents may be used to prepare the peptides of this invention.

The process for synthesizing the cyclic peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). *Angew Chem* 24:799-810 (1985) and Barany et al., *The Peptides, Analysis, Synthesis and Biology*, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, P-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pmc is a preferred protecting group for Arg.

The peptides of the invention described herein were prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin, a 2-chlorotrityl chloride resin or an oxime resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one preferred embodiment the N-terminus group is modified by introduction of an N-acetyl group. In one aspect, a method is employed wherein after removal of the protecting group at the N-terminal, the resin-bound peptide is reacted with acetic anhydride in dichloromethane in the presence of an organic base, such as diisopropylethylamine. Other methods of N-terminus acetylation are known in the art, including solution phase acetylation, and may be employed.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diisopropylethylamine (DIPEA), sym-collidine or N-methylmorpholine (NMM).

The cyclized peptides can then be cleaved from solid phase, using any suitable reagent, such as ethylamine in DCM. The resulting crude peptide is dried and remaining amino acid side chain protecting groups, if any, are cleaved using any suitable reagent, such as trifluoroacetic acid (TFA) in the presence of water and 1,2-ethanedithiol (EDT). The final product is precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Peptides of the present invention have a C-terminus substituted amide derivative or N-alkyl group, and may conveniently be prepared by solid phase synthesis which is commenced from the C-terminal end of the peptide by coupling a protected alpha amino acid to a suitable resin. Such methods for preparing substituted amide derivatives on solid-phase have been described in the art. See, for example, Barn D. R. et al., Synthesis of an array of amides by aluminum chloride assisted cleavage on resin bound esters. *Tetrahedron Letters*, 37:3213-3216 (1996); DeGrado W. F. and Kaiser E. T., Solid-phase synthesis of protected peptides on a polymer bound oxime: Preparation of segments comprising the sequences of a cytotoxic 26-peptide analogue. *J. Org. Chem.*, 47:3258-3261 (1982). Such a starting material can be prepared by attaching an alpha amino-protected amino acid by an ester linkage to a p-benzyloxybenzyl alcohol (Wang) resin or an oxime resin by well known means. The peptide chain is grown with the desired sequence of amino acids, the peptide cyclized and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, and peptides employing an oxime resin may be cleaved by DCM.

Formulation and Utility

The peptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptides of this invention may be synthesized by solid-phase synthesis and purified according to methods known in the art. Any of a number of well-known procedures utilizing a variety of resins and reagents may be used to prepare the peptides of this invention.

Salt Form of Cyclic Peptides.

The cyclic peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of this invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form and the ammonium acetate salt form are especially useful. Where the peptides of this invention include an acidic moiety, suitable pharmaceutically acceptable salts may include alkali metal salts, such as sodium or potassium salts, or alkaline earth metal salts, such as calcium or magnesium salts.

Pharmaceutical Compositions.

The invention provides a pharmaceutical composition that includes a cyclic peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of this invention may be formulated or compounded into pharmaceutical compositions that include at least one cyclic peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of cyclic peptides of this invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another advantageous dosage unit form, sublingual constructs may be employed, such as sheets, wafers, tablets or the like.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides of this invention may be therapeutically applied by means of nasal administration. By "nasal administration" is meant any form of intranasal administration of any of the cyclic peptides of this invention. The peptides may be in an aqueous solution, such as a solution including saline, citrate or other common excipients or preservatives. The peptides may also be in a dry or powder formulation.

The cyclic peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides of this invention may be administered directly into the lung. Intrapulmonary administration may be performed by means of a metered dose inhaler, a device allowing self-administration of a metered bolus of a peptide of this invention when actuated by a patient during inspiration. In one aspect of this embodiment, the cyclic peptide may be in a dried and particulate form, for example particles between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides of this invention may be therapeutically administered by means of an injection, typically a deep intramuscular injection, such as in the gluteal or deltoid muscle, of a time release injectable formulation. In one embodiment, a cyclic peptide of this invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide of this invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a time release injectable formulation. The formulation may be such that an injection is required on a weekly, monthly or other periodic basis, depending on the concentration and amount of cyclic peptide, the bioerosion rate of the polymer, and other factors known to those of skill in the art.

Routes of Administration.

If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount.

In general, the actual quantity of cyclic peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of this invention that is sufficient to therapeutically alleviate sexual dysfunction in a patient, or to prevent or delay onset or recurrence of the sexual dysfunction.

In general, the cyclic peptides of this invention are highly active. For example, the cyclic peptide can be administered at about 0.1, 0.5, 1, 5, 50, 100, 500, 1000 or 5000 µg/kg body weight, depending on the specific peptide selected, the desired therapeutic response, the route of administration, the formulation and other factors known to those of skill in the art.

Therapeutic Application in Males.

The cyclic peptides and pharmaceutical compositions of this invention may be used to treat male sexual dysfunction, including erectile dysfunction or impotence.

Therapeutic Application in Females.

The cyclic peptides and pharmaceutical compositions of this invention may be used to treat female sexual dysfunction, including without limitation sexual arousal disorder.

Diagnostic Application.

The cyclic peptides of this invention may be used for diagnostic purposes, to diagnose causes of erectile dysfunction in males, or sexual dysfunction in mammals generally. Thus, the cyclic peptides may be administered and the erectile reaction of the patient monitored.

Applications for Other Indications.

In addition to treatment of sexual dysfunction, compounds of the current invention may be employed for the treatment of other and additional conditions. These include treatment of obesity, suppression of food intake, induced weight loss, increased energy expenditure, treatment of depression, treatment of anxiety, treatment of diabetes, including maintenance of insulin sensitivity, reduction of voluntary ethanol consumption, and other diseases, conditions and syndromes for which a melanocortin receptor agonist or partial agonist, including specifically an MC3-R or MC4-R agonist or partial agonist, may be efficacious.

Combination Therapy.

It is also possible and contemplated to use C-terminus N-alkyl cyclic peptides of this invention in combination with other drugs or agents, such as for treatment of sexual dysfunction. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. The teachings and disclosure of U.S. patent application Ser. No. 11/139,730, filed May 26, 2005, and entitled "Multiple Agent Therapy for Sexual Dysfunction", are incorporated here by reference as if set forth in full.

The present invention thus provides methods of treating sexual dysfunction, the methods comprising the step of administering to the patient having or at risk of having sexual dysfunction a therapeutically effective amount of a cyclic peptide of this invention in combination with a therapeutically effective amount of a second sexual dysfunction pharmaceutical agent. The cyclic peptide of this invention may be administered simultaneously with, prior to or subsequent to administration with a therapeutically effective amount of a second sexual dysfunction pharmaceutical agent. Preferably the peptide of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of this invention when desired or needed by the patient.

The present invention thus provides methods of treating sexual dysfunction, the methods comprising the step of administering to a patient having or at risk of having sexual dysfunction a therapeutically effective amount of a cyclic peptide of this invention in combination with another compound that is useful in the treatment of sexual dysfunction. In a preferred embodiment of combination therapy the sexual dysfunction is female sexual dysfunction. In an especially preferred embodiment of combination therapy the sexual dysfunction is erectile dysfunction.

The present invention also provides pharmaceutical compositions that comprise a cyclic peptide of this invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; α-adrenergic antagonists; androgens; selective androgen receptor modulators (SARMs); buprorion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Cialis®, a brand of tadalafil. Other PDE-5 inhibitors are disclosed in U.S. patent application Ser. No. 11/139,730, filed May 26, 2005, and entitled "Multiple Agent Therapy for Sexual Dysfunction", incorporated here by reference.

In another embodiment of the composition above, the compound useful for the treatment of sexual dysfunction is an estrogen agonist/antagonist. In one embodiment, the estrogen agonist/antagonist is (−)-cis-6-phenyl-5-[4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of this invention may be used in combination with any known mechanical aids or devices.

The present invention also provides kits for the treatment of sexual dysfunction (including erectile dysfunction), the kits comprising: a first pharmaceutical composition including a cyclic peptide of this invention; a second pharmaceutical composition comprising a second compound useful for the treatment of sexual dysfunction; and, a container for the first and second compositions.

INDUSTRIAL APPLICABILITY

The invention is further illustrated by the following non-limiting examples.

Example 1

Competitive Inhibition Assay Using [$I^{125}$]-NDP-α-MSH

A competitive inhibition binding assay was conducted for selected compounds using membranes prepared from transfected HEK-293 cells expressing hMC3-R, hMC4-R or hMC5-R, and B-16 mouse melanoma cells (containing MC1-R), using respectively 0.4 nM, 0.2 nM, 0.4 nM and 0.1 nM [I$^{125}$]-NDP-α-MSH (New England Nuclear) in 25 mM HEPES buffer containing 2 mM MgCl$_2$, 2 mM CaCl$_2$, and 100 mM NaCl, 0.2% bovine serum albumin and 0.3 mM 1,10 phenanthroline and protease inhibitors at pH 7.5. The assay tube also contained a chosen concentration of the test peptide of this invention, typically a 1 µM concentration, for determining its efficacy in inhibiting the binding of [I$^{125}$]NDP-α-MSH to the receptor. Non-specific binding was measured by complete inhibition of binding of [I$^{125}$]-NDP-α-MSH in the assay with the presence of 1 µM NDP-α-MSH.

The assay mixture was incubated for 60 minutes at 37° C., then filtered and the membranes washed three times with ice cold phosphate buffered saline. The filter was dried and counted in a gamma counter for remaining radioactivity bound to the membranes. 100% specific binding was defined as the difference in radioactivity (cpm) bound to cell membranes in the absence and presence of 1 µM NDP-α-MSH. The cpm obtained in presence of test peptides was normalized with respect to 100% specific binding to determine the percent inhibition of [I$^{125}$]-NDP-α-MSH binding. Each assay was conducted in triplicate. The Ki (nM) of certain peptides of the invention were determined using similar assay protocols and testing peptides over a wider dose range.

Example 2

General Method for EC$_{50}$ Determination in Functional Activity Assay

Functional evaluation of peptides at melanocortin receptors was performed by measuring the accumulation of intracellular cAMP in HEK-293 cells expressing hMC3-R, hMC4-R or hMC5-R, and in B-16 mouse melanoma cells expressing MC1-R. Cells suspended in Earle's Balanced Salt Solution containing 10 mM HEPES (pH 7.5), 5 mM MgCl$_2$, 1 mM glutamine, 0.5% albumin and 0.3 mM 3-isobutyl-1-methyl-xanthine, a phosphodiesterase inhibitor, were plated in 96 well plates at a density of 0.5×10$^5$ cells per well. Cells were incubated with the test peptides in the presence or absence of NDP-α-MSH for 1 hour at 37° C. cAMP levels in the cell lysates were measured using an EIA kit (Amersham). Data analysis and EC$_{50}$ values were determined using nonlinear regression analysis with Prism Graph-Pad software.

Example 3

Functional Status

The agonist/antagonist status with respect to MC1-R, MC4-R and MC5-R of certain peptides of the invention was determined. Antagonistic activity was determined by measuring the inhibition of α-MSH-induced or NDP-α-MSH-induced cAMP levels following exposure to the peptides as in the preceding descriptions.

Assay for Agonist.

Evaluation of the molecules to elicit a functional response in HEK-293 cells expressing hMC4-R for agonistic activity was done by measuring the accumulation of intracellular cAMP following treatment. Confluent HEK-293 cells overexpressing MC4-R receptors were detached by enzyme free cell suspension buffer. Cells were suspended in Earle's Balanced Salt Solution containing 10 mM HEPES (pH 7.5), 1 mM MgCl$_2$, 1 mM glutamine, 0.5% albumin and 0.3 mM 3-isobutyl-1-methyl-phosphodiesterase inhibitor. The cells were plated in a 96 well plate at a density of 0.5×10$^5$ cells per well and pre-incubated for 60 minutes. The cells were then challenged with the test peptides dissolved in dimethylsulfoxide (DMSO) at a concentration range of 0.05-5000 nM in a total assay volume of 200 µL for 1 hour at 37° C. The concentration of DMSO was held at 1% in the assay mixture. NDP-α-MSH was used as the reference agonist. At the end of the incubation period the cells were disrupted by the addition of 50 µL lysis buffer from the cAMP EIA kit (Amersham). Complete rupture of the cells was ensured by pipetting the cells. cAMP levels in the cell lysates were measured after appropriate dilution using the EIA kit (Amersham) method. Data analysis and EC$_{50}$ values were determined by using nonlinear regression analysis with the Prism Graph-Pad software. Peptides at a concentration of 5000 nM with a response ratio compared to NDP-α-MSH of 0.7 and above were classified as full agonists. Peptides with a ratio from 0.1 to 0.7 were classified as partial agonists.

Example 4

Food Intake and Body Weight Change

Change in food intake and body weight is evaluated for selected peptides when administered by an ICV route. Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered food (LabDiet, 5P00 Prolab RMH 3000) is provided ad libitum. For 1 week before treatment, 24-hour food intake and body weight change is recorded to assess a baseline for the group during vehicle treatment. The rats are dosed ICV with vehicle or selected peptides (1-3 nmol). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

Change in food intake and body weight is evaluated for selected peptides administered by IV or IP routes. Male Sprague-Dawley rats are obtained from Taconic (Germantown, N.Y.). Animals are individually housed in conventional plexiglass hanging cages and maintained on a controlled 12 hour on/off light cycle. Water and powdered (LabDiet, 5P00 Prolab RMH 3000) food is provided ad libitum. For 1 week before treatment, 24-hour food intake and body weight change is recorded to assess a baseline for the group during vehicle treatment. The rats are dosed IV or IP with vehicle or selected peptides (0.5-3 mg/kg). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

Example 5

Penile Erection Induction

The ability of peptides to induce penile erection (PE) in male rats was evaluated with selected peptides. Male Sprague-Dawley rats weighing 200-250 g were kept on a 12 hour on/off light cycle with food and water ad libitum. All behavioral studies were performed between 10 a.m. and 5 p.m. Groups of 4-8 rats were administered peptides at a variety of doses via an intravenous (IV) route, and may alternatively be administered peptide by an intracerebroventricular (ICV) route. Immediately after treatment, rats were placed into individual polystyrene cages (27 cm long, 16 cm wide, and 25 cm high) for behavioral observation. Rats administered peptide by an IV route were observed for one hour, and the number of yawns, grooming bouts and PEs are recorded in 10-minute bins. For rats administered peptide by an ICV routes, rats are observed for two hours.

Example 6

Determination of Mass and Nuclear Magnetic Resonance Analysis

The mass values of peptides of the invention were determined using a Waters MicroMass ZQ device utilizing a positive mode. Mass determinations were compared with calculated values and expressed in the form of mass weight plus one (M+1 or M+H).

Proton NMR data was obtained using a Bruker 300 MHz spectrometer. The spectra were obtained after dissolving peptides in a deuterated solvent such as chloroform, DMSO, or methanol as appropriate.

Example 7

Ac-Nle-cyclo(-Asp-His-D-Phe-Arg-Trp-Lys)-NH—CH$_2$—CH$_3$

The peptide Ac-Nle-cyclo(-Asp-His-D-Phe-Arg-Trp-Lys)-NH—CH$_2$—CH$_3$ was synthesized by conventional peptide synthesis methods. The formula weight was determined to be 1166. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 0.11 | 11 | 0.34 | 5 |

| Ki (nM) (AgRP) | |
|---|---|
| MC3-R | MC4-R |
| 9 | 0.15 |

In a cAMP assay for determination of agonist/antagonist status, it was determined that the peptide was an agonist as to MC1-R with an EC$_{50}$ (nm) of 1 and efficacy, relative to NDP-α-MSH, of 0.9, an agonist as to MC3-R with an EC$_{50}$ (nm) of 3 and efficacy, relative to NDP-α-MSH, of 0.9, and an agonist as to MC4-R with an EC$_{50}$ (nm) of 0.6 and efficacy, relative to NDP-α-MSH, of 1.0.

Example 8

Ac-Nle-cyclo(-Asp-His-D-Phe-Arg-Trp-Lys)-N(CH$_3$)$_2$

The peptide Ac-Nle-cyclo(-Asp-His-D-Phe-Arg-Trp-Lys)-N(CH$_3$)$_2$ was synthesized by conventional peptide synthesis methods. The formula weight was determined to be 1166. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 0.01 | 8 | 0.27 | 7 |

| Ki (nM) (AgRP) | |
|---|---|
| MC3-R | MC4-R |
| ND | 0.5 |

In a cAMP assay for determination of agonist/antagonist status, it was determined that the peptide was an agonist as to MC1-R with an EC$_{50}$ (nm) of 1 and efficacy, relative to NDP-α-MSH, of 0.8, an agonist as to MC3-R with an EC$_{50}$ (nm) of 17 and efficacy, relative to NDP-α-MSH, of 0.9, and an agonist as to MC4-R with an EC$_{50}$ (nm) of 0.2 and efficacy, relative to NDP-α-MSH, of 1.0.

Example 9

Ac-Nle-cyclo(-Asp-His-D-Phe-Arg-Nal 1-Lys)-NH—CH$_2$—CH$_3$

The peptide Ac-Nle-cyclo(-Asp-His-D-Phe-Arg-Nal 1-Lys)-NH—CH$_2$—CH$_3$ was synthesized by conventional peptide synthesis methods. The formula weight was determined to be 1177. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 0.07 | 28 | 2 | 63 |

| Ki (nM) (AgRP) | |
|---|---|
| MC3-R | MC4-R |
| ND | 7 |

In a cAMP assay for determination of agonist/antagonist status, it was determined that the peptide was a partial agonist as to MC1-R with an EC$_{50}$ (nm) of 8 and efficacy, relative to NDP-α-MSH, of 0.6, an agonist as to MC3-R with an EC$_{50}$ (nm) of 208 and efficacy, relative to NDP-α-MSH, of 1.0, and a partial agonist as to MC4-R with an EC$_{50}$ (nm) of 0.2 and efficacy, relative to NDP-α-MSH, of 0.6.

Example 10

Ac-Nle-cyclo(-Asp-Trp-D-Phe-Arg-Nal 1-Lys)-N(CH$_3$)$_2$

The peptide Ac-Nle-cyclo(-Asp-Trp-D-Phe-Arg-Nal 1-Lys)-N(CH$_3$)$_2$ was synthesized by conventional peptide synthesis methods. The formula weight was determined to be 1226. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 12 | 231 | 38 | 31 |

| Ki (nM) (AgRP) | |
|---|---|
| MC3-R | MC4-R |
| >1,000 | 50 |

In a cAMP assay for determination of agonist/antagonist status, it was determined that the peptide was an agonist as to MC1-R with an EC$_{50}$ (nm) of 2296 and efficacy, relative to NDP-α-MSH, of 1.1, was inactive as to MC3-R, and was an agonist as to MC4-R with an EC$_{50}$ (nm) of 272 and efficacy, relative to NDP-α-MSH, of 0.8.

Example 11

Ac-Nle-cyclo(-Asp-His-D-Phe-Arg-Nal 1-Lys)-N(CH$_3$)$_2$

The peptide Ac-Nle-cyclo(-Asp-His-D-Phe-Arg-Nal 1-Lys)-N(CH$_3$)$_2$ was synthesized by conventional peptide synthesis methods. The formula weight was determined to be 1177. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 0.39 | 111 | 5 | 50 |

| Ki (nM) (AgRP) | |
|---|---|
| MC3-R | MC4-R |
| >1,000 | 10 |

In a cAMP assay for determination of agonist/antagonist status, it was determined that the peptide was an agonist as to MC1-R with an EC$_{50}$ (nm) of 15 and efficacy, relative to NDP-α-MSH, of 0.8, an agonist as to MC3-R with an EC$_{50}$ (nm) of 394 and efficacy, relative to NDP-α-MSH, of 1.1, and an agonist as to MC4-R with an EC$_{50}$ (nm) of 44 and efficacy, relative to NDP-α-MSH, of 0.7.

Example 12

Ac-cyclo(-Asp-His-D-Phe-Arg-Trp-Lys)-NH—CH$_2$—CH$_3$

The peptide Ac-cyclo(-Asp-His-D-Phe-Arg-Trp-Lys)-NH—CH$_2$—CH$_3$ was synthesized by conventional peptide synthesis methods. The formula weight was determined to be 1053. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 5 | 84 | 6 | >1,000 |

| Ki (nM) (AgRP) | |
|---|---|
| MC3-R | MC4-R |
| 457 | 11 |

In a cAMP assay for determination of agonist/antagonist status, it was determined that the peptide was a partial agonist as to MC1-R with an EC$_{50}$ (nm) of 64 and efficacy, relative to NDP-α-MSH, of 0.6, an agonist as to MC3-R with an EC$_{50}$ (nm) of 283 and efficacy, relative to NDP-α-MSH, of 1.0, and a partial agonist as to MC4-R with an EC$_{50}$ (nm) of 3 and efficacy, relative to NDP-α-MSH, of 0.6.

Example 13

Ac-cyclo(-Asp-His-D-Phe-Arg-Trp-Lys)-N(CH$_3$)$_2$

The peptide Ac-cyclo(-Asp-His-D-Phe-Arg-Trp-Lys)-N(CH$_3$)$_2$ was synthesized by conventional peptide synthesis methods. The formula weight was determined to be 1053. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 2 | 154 | 12 | >1,000 |

| Ki (nM) (AgRP) | |
|---|---|
| MC3-R | MC4-R |
| ND | 18 |

In a cAMP assay for determination of agonist/antagonist status, it was determined that the peptide was an agonist as to MC1-R with an $EC_{50}$ (nm) of 151 and efficacy, relative to NDP-α-MSH, of 0.7, an agonist as to MC3-R with an $EC_{50}$ (nm) of 1251 and efficacy, relative to NDP-α-MSH, of 1.3, and a partial agonist as to MC4-R with an $EC_{50}$ (nm) of 5.0 and efficacy, relative to NDP-α-MSH, of 0.6.

Example 14

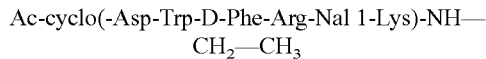

The peptide Ac-cyclo(-Asp-Trp-D-Phe-Arg-Nal 1-Lys)-NH—CH$_2$—CH$_3$ was synthesized by conventional peptide synthesis methods. The formula weight was determined to be 1113. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 166 | 886 | 45 | >2,000 |

| Ki (nM) (AgRP) | |
|---|---|
| MC3-R | MC4-R |
| >10,000 | 71 |

In a cAMP assay for determination of agonist/antagonist status, it was determined that the peptide was inactive as to MC1-R, inactive as to MC3-R, and an agonist as to MC4-R with an $EC_{50}$ (nm) of 698 and efficacy, relative to NDP-α-MSH, of 0.7.

Example 15

Ac-cyclo(-Asp-Trp-D-Phe-Arg-Nal 1-Lys)-N(CH$_3$)$_2$

The peptide Ac-cyclo(-Asp-Trp-D-Phe-Arg-Nal 1-Lys)-N(CH$_3$)$_2$ was synthesized by conventional peptide synthesis methods. The formula weight was determined to be 1177. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 215 | 964 | 122 | 549 |

| Ki (nM) (AgRP) | |
|---|---|
| MC3-R | MC4-R |
| >3,000 | 233 |

In a cAMP assay for determination of agonist/antagonist status, it was determined that the peptide was inactive as to MC1-R, inactive as to MC3-R, and an agonist as to MC4-R with an $EC_{50}$ (nm) of 1543 and efficacy, relative to NDP-α-MSH, of 0.9.

Example 16

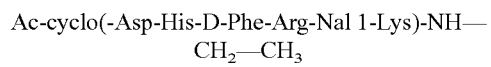

The peptide Ac-cyclo(-Asp-His-D-Phe-Arg-Nal 1-Lys)-NH—CH$_2$—CH$_3$ was synthesized by conventional peptide synthesis methods. The formula weight was determined to be 1064. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 18 | 462 | 157 | 937 |

| Ki (nM) (AgRP) | |
|---|---|
| MC3-R | MC4-R |
| >2,000 | 284 |

In a cAMP assay for determination of agonist/antagonist status, it was determined that the peptide was an agonist as to MC1-R with an $EC_{50}$ (nm) of 6410 and efficacy, relative to NDP-α-MSH, of 0.9, an agonist as to MC3-R with an $EC_{50}$ (nm) of 6211 and efficacy, relative to NDP-α-MSH, of 0.8, and an agonist as to MC4-R with an $EC_{50}$ (nm) of 500 and efficacy, relative to NDP-α-MSH, of 1.1.

Example 17

Ac-cyclo(-Asp-His-D-Phe-Arg-Nal 1-Lys)-N(CH$_3$)$_2$

The peptide Ac-cyclo(-Asp-His-D-Phe-Arg-Nal 1-Lys)-N(CH$_3$)$_2$ was synthesized by conventional peptide synthesis methods. The formula weight was determined to be 1064. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 40 | >10,000 | 92 | >10,000 |

| Ki (nM) (AgRP) | |
|---|---|
| MC3-R | MC4-R |
| ND | ND |

In a cAMP assay for determination of agonist/antagonist status, it was determined that the peptide was an agonist as to MC1-R with an EC$_{50}$ (nm) of 2364 and efficacy, relative to NDP-α-MSH, of 1.0, a partial agonist as to MC3-R with an EC$_{50}$ (nm) of >1000 and efficacy, relative to NDP-α-MSH, of 0.4, and an agonist as to MC4-R with an EC$_{50}$ (nm) of 91 and efficacy, relative to NDP-α-MSH, of 0.93.

Example 18

Ac-Nle-cyclo(-Asp-Trp-D-Phe-Arg-Nal 1-Lys)-NH—CH$_2$—CH$_3$

The peptide Ac-Nle-cyclo(-Asp-Trp-D-Phe-Arg-Nal 1-Lys)-NH—CH$_2$—CH$_3$ was synthesized by conventional peptide synthesis methods. The formula weight was determined to be 1226. Competitive inhibition testing and Ki (nM) of the peptide was measured following the method of Example 1. Functional status of the peptide was determined following the methods of Examples 2 and 3.

| Ki (nM) (NDP-α-MSH) | | | |
|---|---|---|---|
| MC1-R | MC3-R | MC4-R | MC5-R |
| 3 | 77 | 9 | 47 |

| Ki (nM) (AgRP) | |
|---|---|
| MC3-R | MC4-R |
| ND | 26 |

In a cAMP assay for determination of agonist/antagonist status, it was determined that the peptide was a partial agonist as to MC1-R with an EC$_{50}$ (nm) of 397 and efficacy, relative to NDP-α-MSH, of 0.3, a partial agonist as to MC3-R with an EC$_{50}$ (nm) of 1823 and efficacy, relative to NDP-α-MSH, of 0.2, and a partial agonist as to MC4-R with an EC$_{50}$ (nm) of 120 and efficacy, relative to NDP-α-MSH, of 0.6.

Example 19

Penile Erection Induction Studies

Selected peptides were tested as in Example 5. Peptide was administered by IV routes, and used at dose levels ranging from 1 µg/kg to 1000 µg/kg. All studies were conducted employing groups of 6 rats, with the mean number of PEs per rat recorded as well as the percentage of rats (of the total group) exhibiting at least one PE during the observation period. Controls employed were saline (negative control or baseline response) and Ac-Nle-cyclo(-Asp-His-D-Phe-Arg-Trp-Lys)-OH (positive control). Peptides of Examples 7, 8, 9, 11, 13 and 17 each had a PE effect at a peak dose of 1000 µg/kg administered by an IV route, with 100% of rats exhibiting at least one PE, and with between 3.6 and 10.3 mean PEs per rat. The effect with the peptide of Example 11 was the same at a peak dose of 300 µg/kg administered by an IV route. The peptide of Example 12 had a PE effect at a peak dose of 300 µg/kg administered by an IV route, with 83% of rats exhibiting at least one PE, and with 2.5 mean PEs per rat. Rats administered the saline negative control had between 0.16 and 1.5 mean PEs per rat, with between 16.7% and 100% of rats exhibiting at least one PE. Rats administered 1000 µg/kg of positive control Ac-Nle-cyclo(-Asp-His-D-Phe-Arg-Trp-Lys)-OH by an IV route had between 1.67 and 6 mean PEs per rat, with between 66.7% and 100% of rats exhibiting at least one PE.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

We claim:

1. A cyclic peptide of the structural formula:

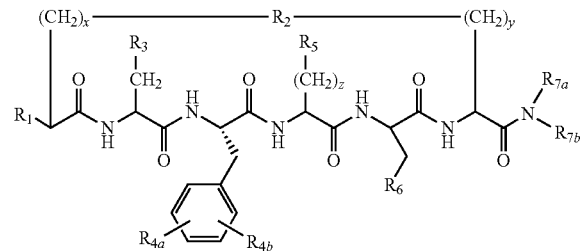

wherein:

$R_1$ is H, $NH_2$,

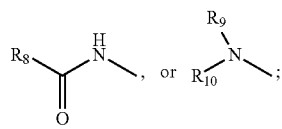

$R_2$ is —C(=O)—NH—, —NH—C(=O)—, —S—, or —S—S—;

$R_3$ is 4-imidazolyl or 3-indolyl;

$R_{4a}$ and $R_{4b}$ are each optional ring substituents, and when one or both are present, are the same or different and independently hydroxyl, halogen, alkyl, or aryl groups attached directly or through an ether linkage;

$R_5$ is —$NH_2$ or —NH(C=NH)$NH_2$;

$R_6$ is 1- or 2-naphthyl or 3-indolyl, optionally with one or two ring substituents, and when one or both ring substitutents are present, are the same or different and independently hydroxyl, halogen, alkyl, or aryl groups attached directly or through an ether linkage;

$R_{7a}$ and $R_{7b}$ are each independently H or a $C_1$ to $C_4$ linear or branched alkyl chain, on the proviso that both $R_{7a}$ and $R_{7b}$ are not H;

$R_8$ is H, $NH_2$, a lower aliphatic $C_1$ to $C_4$ branched or linear alkyl chain, a $C_1$ to $C_4$ aralkyl, or a $C_1$ to $C_4$ omega amino aliphatic chain;

$R_9$ is H, a lower aliphatic $C_1$ to $C_4$ branched or linear alkyl chain, a $C_1$ to $C_4$ aralkyl, or a $C_1$ to $C_4$ omega amino aliphatic chain;

$R_{10}$ is an aliphatic L- or D-amino acid, an N-acylated L- or D-amino acid or a linear or branched $C_1$ to $C_{17}$ alkyl, aryl, heteroaryl, alkene, alkenyl, or aralkyl chain;

x is 1 to 4, and y is 1 to 5, provided that x+y is 2 to 7; and z is 1 to 5.

2. The cyclic peptide of claim 1 of the structural formula:

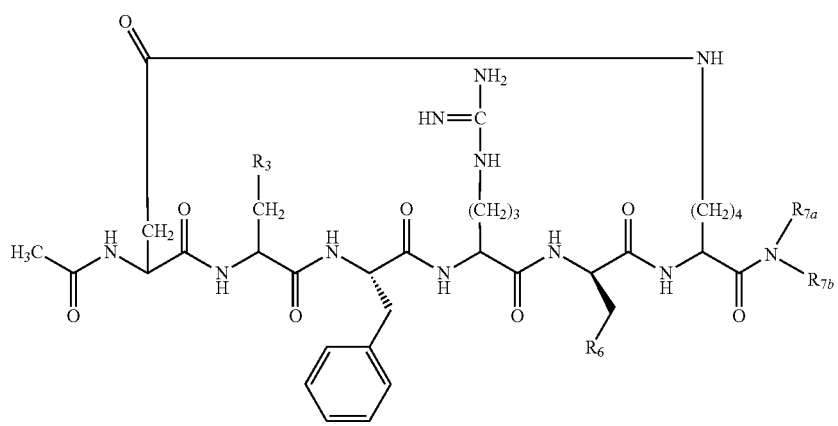

(II)

wherein $R_3$, $R_6$, $R_{7a}$ and $R_{7b}$ are as defined in claim 1.

3. The cyclic peptide of claim 2 which is:

```
Ac-cyclo(-Asp-His-D-Phe-Arg-Trp-Lys)-N(CH₃)₂,
Ac-cyclo(-Asp-His-D-Phe-Arg-Trp-Lys)-NH-CH₂-CH₃,
Ac-cyclo(-Asp-Trp-D-Phe-Arg-Nal 1-Lys)-NH-CH₂-CH₃,
Ac-cyclo(-Asp-Trp-D-Phe-Arg-Nal 1-Lys)-N(CH₃)₂,
Ac-cyclo(-Asp-His-D-Phe-Arg-Nal 1-Lys)-NH-CH₂-CH₃,
or
Ac-cyclo(-Asp-His-D-Phe-Arg-Nal 1-Lys)-N(CH₃)₂.
```

4. The cyclic peptide of claim 1 of the structural formula:

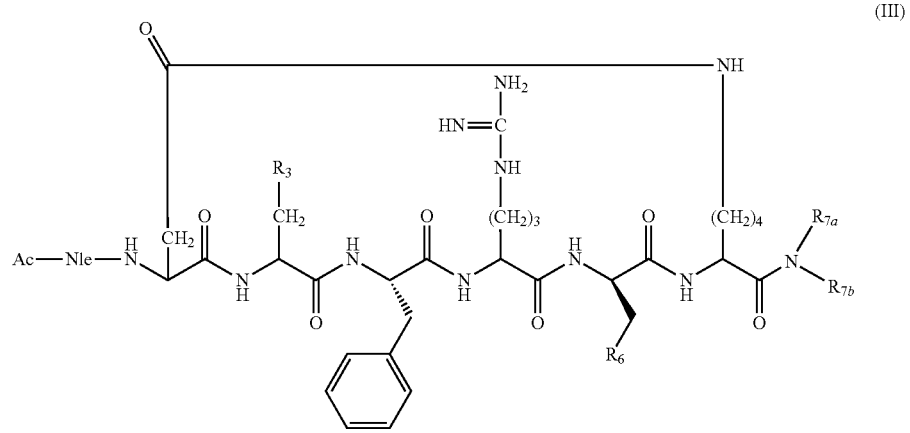

(III)

wherein $R_3$, $R_6$, $R_{7a}$ and $R_{7b}$ are as defined in claim 1.

5. The cyclic peptide of claim 4 which is:

```
Ac-Nle-cyclo(-Asp-His-D-Phe-Arg-Trp-Lys)-
  NH-CH₂-CH₃,

Ac-Nle-cyclo(-Asp-His-D-Phe-Arg-Trp-Lys)-N(CH₃)₂,

Ac-Nle-cyclo(-Asp-His-D-Phe-Arg-Nal 1-Lys)-
  NH-CH₂-CH₃,

Ac-Nle-cyclo(-Asp-Trp-D-Phe-Arg-Nal 1-Lys)-
  N(CH₃)₂,

Ac-Nle-cyclo(-Asp-His-D-Phe-Arg-Nal 1-Lys)-
  NH-CH₂-CH₃,
or

Ac-Nle-cyclo(-Asp-Trp-D-Phe-Arg-Nal 1-Lys)-
  NH-CH₂-CH₃.
```

6. The cyclic peptide of claim 1 of the structural formula:

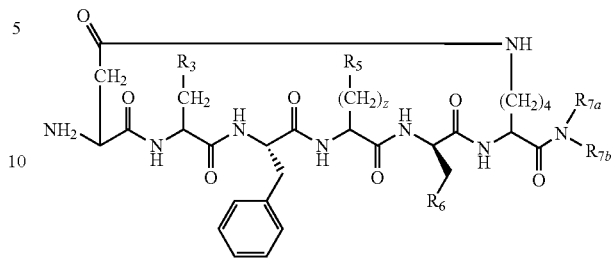

(IV)

wherein $R_3$, $R_5$, $R_6$, $R_{7a}$, $R_{7b}$ and z are as defined in claim 1.

7. The cyclic peptide of claim 6 which is:

```
H-cyclo(-Asp-His-D-Phe-Arg-Trp-Lys)-N(CH₃)₂,
H-cyclo(-Asp-His-D-Phe-Arg-Trp-Lys)-NH-CH₂-CH₃,
H-cyclo(-Asp-Trp-D-Phe-Arg-Nal 1-Lys)-NH-CH₂-CH₃,
H-cyclo(-Asp-Trp-D-Phe-Arg-Nal 1-Lys)-N(CH₃)₂,
H-cyclo(-Asp-His-D-Phe-Arg-Nal 1-Lys)-NH-CH₂-CH₃,
or
H-cyclo(-Asp-His-D-Phe-Arg-Nal 1-Lys)-N(CH₃)₂.
```

8. A pharmaceutical preparation, comprising a cyclic peptide of claim 1 or a pharmaceutically acceptable salt thereof, and a pharmaceutically acceptable carrier.

9. A method of treating sexual dysfunction, comprising administering a pharmaceutically sufficient amount of a pharmaceutical preparation of claim 8 to a mammal.

10. A cyclic hexapeptide with a C-terminus N-alkyl group, wherein the N-alkyl group comprises one or two $C_1$ to $C_4$ linear or branched alkyl chains, the hexapeptide containing the core sequence His-D-Phe-X—Y or Trp-D-Phe-X—Y, wherein X is an L-amino acid selected from the group consisting of Arg, Lys, Orn, Harg and Hlys and Y is an L- or D-amino acid selected from the group consisting of Nal 1, Nal 2 and Trp, and wherein any aromatic ring in the core sequence may optionally include one or two ring substituents, and when one or both ring substitutents are present, are the same or different and independently hydroxyl, halogen, alkyl, or aryl groups attached directly or through an ether linkage.

11. The cyclic hexapeptide of claim 10 with an N-terminus Ac or $NH_2$ group.

12. The cyclic hexapeptide of claim 10 wherein the hexapeptide is cyclized by formation of an amide bond between an amino group of a side chain of an amino acid in the 1 position or an amino group of the N-terminus group of the amino acid in the 1 position and a side chain carboxyl group of an amino acid residue at the 6 position.

13. The cyclic hexapeptide of claim 10, wherein the hexapeptide is cyclized by formation of an amide bond between a side chain carboxyl group of an amino acid residue in the 1 position and an amino group of a side chain of an amino acid at the 6 position.

14. The cyclic hexapeptide of claim 10, wherein the hexapeptide is cyclized by formation of a covalent bond comprising an amide, disulfide, thioether, Schiff base, reduced Schiff base, imide, secondary amine, carbonyl, urea, hydrazone or oxime bond.

15. The cyclic hexapeptide of claim 10 wherein the core sequence is in the 2 to 5 positions and is His-D-Phe-X-Nal 1, and is cyclized through the amino acids in the 1 and 6 positions.

16. The cyclic hexapeptide of claim 10 wherein the core sequence is in the 2 to 5 positions and is Trp-D-Phe-X-Nal 1, and is cyclized through the amino acids in the 1 and 6 positions.

17. The cyclic hexapeptide of claim 10 wherein the core sequence is in the 2 to 5 positions and is His-D-Phe-X-Nal 2, and is cyclized through the amino acids in the 1 and 6 positions.

18. The cyclic hexapeptide of claim 10 wherein the core sequence is in the 2 to 5 positions and is Trp-D-Phe-X-Nal 2, and is cyclized through the amino acids in the 1 and 6 positions.

19. The cyclic hexapeptide of claim 10 wherein the core sequence is in the 2 to 5 positions and is His-D-Phe-X-Trp, and is cyclized through the amino acids in the 1 and 6 positions.

20. The cyclic hexapeptide of claim 10 wherein D-Phe is selected from the group consisting of D-isomers of Phe(2-Cl), Phe(3-Cl), Phe(4-Cl), Phe(5-Cl), Phe(2,4-diCl), Phe(2,4-diF), Phe(3,4-diCl), Phe(4-$NO_2$), Phe(4-Me), Phe(4-OMe), Phe(4-F), Phe(4-Br), Phe(4-$CF_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-$CF_3$), Phe(4-CN) and Phe(3,4-di-OMe).

* * * * *

```
                          SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: alpha-melanocyte stimulating hormone core
      messenger sequence

<400> SEQUENCE: 1

His Phe Arg Trp
1
```